United States Patent
Kepler et al.

[11] Patent Number: 6,105,430
[45] Date of Patent: Aug. 22, 2000

[54] INSPECTION OF CONCRETE STRUCTURES USING SONIC TOMOGRAPHY

[75] Inventors: William F. Kepler, Golden, Colo.; Leonard J. Bond, Richland, Wash.

[73] Assignee: The United States of America as represented by the Secretary of the Interior, Washington, D.C.

[21] Appl. No.: 09/109,742

[22] Filed: Jul. 2, 1998

[51] Int. Cl.[7] .................................................. G01N 29/04
[52] U.S. Cl. .............................. 73/594; 73/12.01; 73/598
[58] Field of Search ............................. 73/594, 598, 584, 73/588, 12.01

[56] References Cited

U.S. PATENT DOCUMENTS

| | | | |
|---|---|---|---|
| 4,163,393 | 8/1979 | Gotierrez et al. ........................ | 73/588 |
| 4,429,575 | 2/1984 | Akishika ................................... | 73/598 |
| 5,165,270 | 11/1992 | Sansalone et al. ....................... | 73/594 |

OTHER PUBLICATIONS

J. Krautkramer et al., *Ultrasonic Testing of Materials*(Springer–Verlag, New York, 1983), pp. 558–563, 1983.

*Primary Examiner*—John E. Chapman
*Attorney, Agent, or Firm*—E. Philip Koltos

[57] ABSTRACT

An acoustic travel time tomography system enables determining of physical properties of a dam, or a like concrete mass. The system includes a plurality of acoustic sensors, positioned on the dam at a plurality of spaced sensor locations which are known relative to each other, for producing output data responsive to the detection thereby of acoustic waves generated in the dam. An impact source produces an impact at an impact location which is known relative to the sensor locations so as to generate acoustic waves in the dam for detection by the sensors. A data processing unit acquires output data from the sensors produced responsive to acoustic waves generated by the impact source and analyzes this output data, together with data related to the relative locations of the sensors and the impact source, to determine physical properties of the dam.

20 Claims, 2 Drawing Sheets

INSPECTION OF CONCRETE STRUCTURES USING SONIC TOMOGRAPHY

FIELD OF THE INVENTION

The present invention relates to inspection devices, and more particularly, to inspection devices and methods using sonic tomography to evaluate the structural integrity of concrete structures such as dams.

BACKGROUND OF THE INVENTION

The primary focus in evaluating a large concrete structure, such as a dam, is to determine the ability of the structure to withstand natural disasters such as a major earthquake or serious flooding. The reaction of the structure depends on the mechanical strength developed throughout the complex discontinuous mass of the structure. Presently used construction techniques, combined with normal loading conditions, ensure that most defects in a large concrete dam structure will develop in horizontal planes along construction joints, also known as lift-lines. The survival of a dam under extreme loading conditions often depends on the strength developed across these construction joints or lift-lines.

The traditional method for determining the strength of a concrete dam is to extract large diameter core samples drilled from the top of the dam down to the foundation, which samples are then destructively tested to determine the strength and elastic modulus thereof. These material data are then used in a finite element model to simulate responses of the dam structure to various loading conditions. The parameters required for finite element models include the modulus of elasticity, strength, density, and Poisson's ratio. The location and extent of any defects within the structure are also required. Depending on the size of the structure, two to four drill holes are cored down to the foundation, often a distance of more than 90 meters (300 feet). Large diameters cores, 250–300 millimeters (10 to 12 inches), are required to provide representative samples. It will be appreciated that extracting this amount of large diameter concrete cores is very expensive. In addition, although a coring program of this magnitude is considered sufficient, it only samples a very small percentage of the volume of the dam's structure, typically less than 0.1%. This procedure cannot, therefore, be expected to locate most local anomalies, such as regions of disbonded lift-lines or cracks. A new testing procedure is required which will provide a more thorough evaluation of the physical properties of the structure, and preferably one which is less expensive than a full coring program.

SUMMARY OF THE INVENTION

In general terms, the inspection approach of the present invention combines aspects of ultrasonic nondestructive testing of small concrete structures, nondestructive evaluation of interfaces, and shallow seismic surveying to create a new method and system. As discussed below, the invention can be used alone or in conjunction with a reduced coring program.

In general, acoustic testing can provide reliable estimates of the modulus of elasticity and compressive strength of hardened concrete. However, the present invention uses a sparse array of receivers, and an associated impact or impulse source, to not only determine both local and global bulk modulus and strength values of a structure, but also to detect cracks, voids, and other anomalies within the structure. Commonly used construction techniques, combined with typical loading conditions, ensure that most defects in a mass of concrete, such as a large concrete dam, will be in horizontal planes along lift-lines. For older dams it is expected that "tweak zones" in lift-lines will have developed into complete delaminations. Thus, the inspection problem is simplified to one of the detection and mapping of cracked or delaminated zones in lift-lines and the acoustic travel time tomography system and method of the present invention permits this to be done.

In accordance with one aspect of the invention, an acoustic travel time tomography system is provided for determining physical properties of a dam or like structural mass, the system comprising: a plurality of acoustic sensors, positioned on the dam at a plurality of spaced sensor locations which are known relative to each other, for producing output data responsive to the detection thereby of acoustic waves generated in the dam; an impact or impulse source for producing an impact at an impact location which is known relative to the sensor locations so as to generate acoustic waves in the dam for detection by the sensors; and data processing means for acquiring output data from the sensors produced responsive to acoustic waves generated in the dam by the impact source and for analyzing the output data, together with data related to the relative locations of the sensors and the impact source, to determine physical properties of the dam.

Preferably, the data processing means includes a computer having an optional modem.

The sensors are not typically paired and are advantageously spaced apart about 1.5 meters (10 feet). In an advantageous implementation where the dam is a concrete gravity dam and sensor paris are used, the sensor pairs are positioned 1.5 meters apart along a downstream base of the dam in rows of 90 meters in length, the rows are positioned three meters horizontally along the downstream base of the dam, and at least two additional sensors are placed along a top face of the dam at positions 0.9 meters and 1.5 meters from said downstream base. In this implementation, the sensor pairs are preferably located 1.2 meters from the intersection of the top face and the downstream base of the dam. In general, the spacing of the sensors at the top of the dam will vary with the dam structure.

In a preferred embodiment, the impact source comprises a sledge hammer or other impactor, and an accelerometer connected to the impactor. A steel plate is advantageously provided for striking by the sledge hammer or other impactor. Preferably, the impactor strikes the plate at a frequency between 1 and 50 kilohertz. Advantageously, the impactor is a 3.6 kilogram sledge hammer and the plate is 100 millimeters square and 25 millimeters thick. Preferably, the plate is positioned at impact source positions which are, respectively, 1.2 meters, 1.8 meters, and 2.4 meters from the downstream base, although the location of impact positions will vary with the dam structure.

In accordance with a further aspect of the invention, a method is provided for determining the locations of physical anomalies of a concrete dam or like mass structure, the method comprising the steps of: positioning a plurality of acoustic sensors on a surface of the dam at sensor locations which are spaced apart at known distances relative to each other so that the sensors can receive sonic waves produced in the dam and can produce output data responsive thereto; positioning an impact means for impacting the dam at an impact position which is known relative to the sensor location; activating the impact means to generate a plurality of sonic waves which travel through the dam so that the sonic waves can be received by the plurality of sensors; and monitoring the output data produced by the sensors to detect which of the sensors receive the sonic waves and to determine, based on the known relative positions of the sensors and the impact means, travel times of the sonic waves to the sensors receiving the sonic waves so as to determine the locations of physical anomalies in the dam.

Preferably, the method further comprises repositioning the impact means at different locations on the surface of the dam.

The monitoring of the sensors preferably comprises storing the output data produced by the sensors on a computer, grouping the output data into sets, removing erroneous or anomalous data from the sets (such as that produced by inoperative or malfunctioning sensors), using the computer to provide defect detection and forming a graphical representation of the physical anomalies.

The monitoring of the sensors preferably further comprises determining the time of first arrival of each of the sonic waves, reviewing each wave to determine the time of arrival of a corresponding compressive wave, and computing the travel time of said compressive wave to produce a computed travel time. The computed travel time, and the distances between the impact position (or positions) and the sensor positions, are then used to determine the wave velocity of the sonic waves traveling between the impact position and the sensor positions.

Advantageously, the method further comprising correlating the results of determining the physical anomalies with destructive strength test results, the destructive strength test results preferably being produced by core sampling.

The sonic waves are preferably generated by impacting a hammer on a plate at a frequency rate between 1 and 50 kilohertz.

Preferably, the method further comprises mapping areas surrounding the areas or locations of physical anomalies that have previously been determined, with a second plurality of sensors positioned more closely together than the first mentioned plurality of sensors.

Other features and advantages of the invention will be set forth in, or apparent from, the following detailed description of preferred embodiments of the invention.

DETAILED DESCRIPTION OF THE PREFERRED EMBODIMENTS

Figure 1:
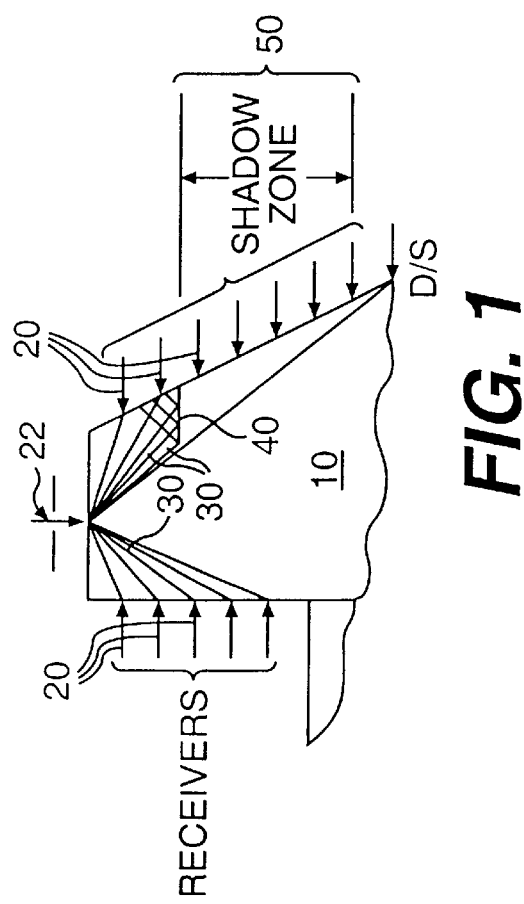
FIG. 1 is a schematic representation of the major components of the inspection system of the present invention in place on a dam.

Referring to FIG. 1, there is shown a large concrete mass 10, in this case a dam, wherein an array of receivers, indicated by arrows 20 are positioned at receiver locations along the dam 10 which are spaced apart at known distances or spacings relative to each other. An impact device 22, such as an impulse source, for impacting the dam 10 is located at the top of dam 10. Impulse source 22 is used to generate an acoustic pulse that has direct waves, as indicated at 30, that will not pass through a major crack 40. Such waves, in effect, create a shadow zone 50 in the area of the lower receivers 20 on the back side of dam 10. In this regard, the only waves 30 that will be received by receivers 20 immediately below the crack 40 will be scattered pulses and tip-diffracted waves, both of which will have clearly identifiable travel time delays when compared with the expected travel time of direct waves 30. When the relative position of the source 22 and receivers 20 are varied, and a ray analysis is employed, the travel times can be used in a tomographic inversion scheme to estimate the penetration of crack 30 through the thickness of the dam 10 using the methods described in "Evaluation of Concrete Using Acoustic Tomography" by Schuller, M. P. and Atkinson, R. H. in *Review of Progress in Quantitative Non-Destructive Evaluation* Ed. D. O. Thompson and D. Chimenti. Vol. 14, Plenum, New York, pages 2215–2222, incorporated herein by reference.

Figure 2:
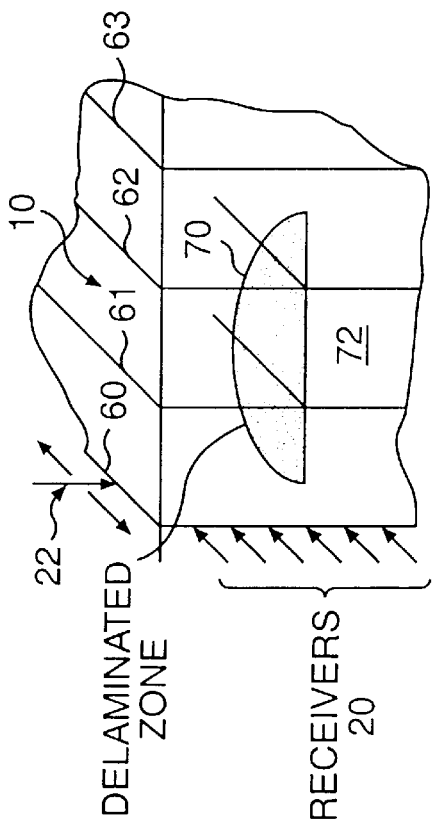
FIG. 2 is a perspective view of a portion of the dam of FIG. 1.

In an advantageous exemplary embodiment, the receivers 20 were set on 3 meter (10 foot) centers along lines down the front of dam 10 to detect the presence of anomalous zones. Such a zone, in this case a delamination zone, is indicated at 70 in FIG. 2, wherein a plurality of lines of data are taken at successive lateral positions 60, 61, 62 and 63 along dam 10 are used to map the joint condition and any cracked area of various existing lift-lines. Once detected and located, the anomalous or defective zones in the lift-lines, such as delamination zone 70, are then characterized using receivers in an increasingly dense array to increase the number of data points, and hence the resolution of map. The coarseness of the mesh of the finite element model used for a dam strength/safety evaluation will ultimately determine the required level of characterization, and therefore the number of data points required. Current finite element analysis techniques employ elements that are typically about 15- by 15-meter (50- by 50-foot) rectangular blocks which are one-half the thickness of the dam. Obviously, the denser the data point grid, the better the data will be but the more costly the testing and modelling of the dam.

In order to estimate the physical properties of a large concrete dam, the results of acoustic tomography obtained according to the method of the present invention can be correlated with destructive strength test results obtained by any of the traditional methods such as coring. The nondestructive measurements using the method of the present invention are made in the frequency range from about 1 to 50 kilohertz depending on the size and attenuation characteristics of the structure 10 and the impulse source 22 employed. Data can initially be taken using a relatively widely spaced array of receivers 20 spaced every 1.5 meters (5 feet) going down a front face, denoted 72 in FIG. 2, of dam 10. These arrays of receivers 20 are up to 90 meters (300 feet) long and are set in lines spaced every 3 meters (10 feet) horizontally.

As the distance between source 22 and an individual array of receivers 20 increases, the arrival time is increasingly delayed. The velocity can be determined by dividing the arrival time by the distance between source 22 and each array receiver 20. By correlating the velocity with destruction strength tests, an estimate for the strength and modulus of elasticity can be determined using a well established relationship. The results of this testing can help determine the best locations to drill core samples that will provide the most data for critical parts of the structure 10.

A discussion of some of the background laboratory work done preparatory to the method of the present invention is found in Kepler, W. F., and Bond, L. J. "Improved Assessment of Concrete Dams Using Sonic Tomography" in *Review of Progress in Quantitative Nondestructive Evaluation*. Vol. 15. Plenum, New York, pages 1807–1814, (1995) incorporated herein by reference. To provide a full scale evaluation, a portion of Barker Dam, above Boulder Colorado was tested since Barker Dam is known to contain horizontal cracked lift-lines. Barker Dam was chosen because of its location, ease of access, simple geometry, and its design and construction are similar to those of structures that will be examined in the future.

Barker Dam is a cyclopean mass concrete gravity dam originally-constructed in 1909. It is 53.5 meters (175 feet) high, and 220 meters (720 feet) wide. The thickness across the top is 6.7 meters (22 feet), and across the bottom the thickness is 34.4 meters (113 feet). As was typical of the time, the concrete was placed in lifts that ranged in thickness from 0.9 to 1.2 meters (3 to 4 feet). The concrete had a maximum size aggregate of 63.5 mm (2½ inches), with the addition of "plums, " which are large rocks weighing anywhere from 10 to 140 kilograms (25 to 300 pounds). Joint preparation between lifts was minimal, and was comprised of sweeping with a broom and placing a low strength grout of cement and water on top of the lift prior to placing the subsequent lift. This method of joint preparation almost always ensures a poor bond between lifts.

In 1946, improvements were made to the upstream face to reduce leakage through the structure. Between 1.5 to 2.4 meters (5 to 8 feet) of aggregate were placed between the dam and a permanent form made of 150 millimeters (6 inch) thick precast concrete. Then the aggregate was grouted in place. In 1986, further modifications were made to reduce the possibility of failure during a seismic event due to low strength across the lift-lines and between the dam and the foundation. The dam was post tensioned using large high-strength cables going from the top of the structure into the foundation, and from midway down the front face into the foundation. To avoid interference caused by the post tension cables and the grouted aggregate, only the downstream (D/S) half of the Barker Dam structure was tested. Baker Dam was constructed in 14 vertical blocks, each approximately 15 meters (48 feet) wide of which blocks nos. 4 and 5 were tested using the method of the present invention. Both blocks nos. 4 and 5 have visible horizontal cracks on the downstream face. The downstream face of no. block 5 has more weathering, probably due to freeze-thaw action.

Figure 3:
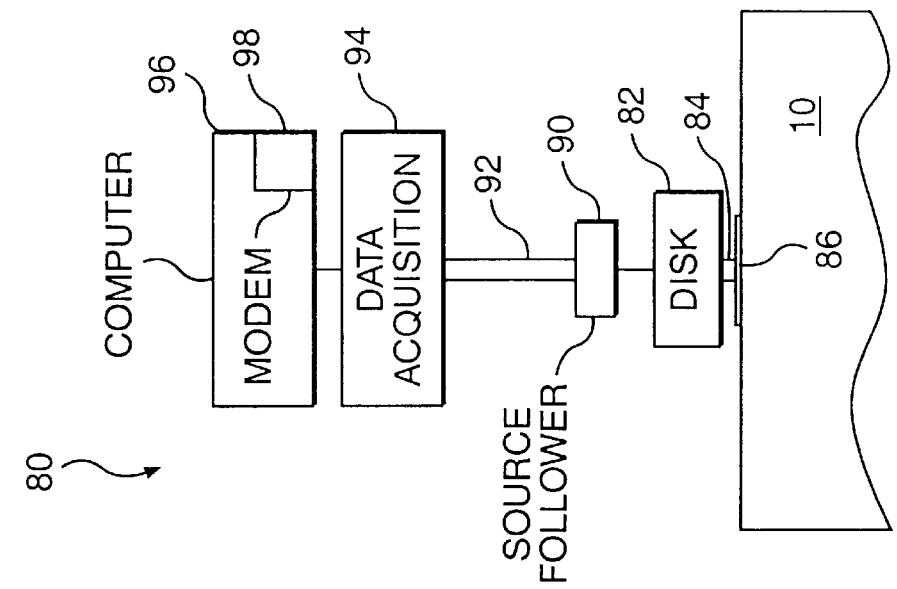
FIG. 3 is a schematic block diagram representation of a preferred embodiment of the receivers of FIGS. 1 and 2.

Referring to FIG. 3, there is illustrated a 20 channel transducer system 80 used in the testing referred to above. The sensors or receivers each comprise a piezoelectric PZT type 5*a* disk 82, with a micro-dot connector 84, mounted on a copper foil 86. The disk 82 is encapsulated in copper to provide electrical shielding. Each disk 92 is attached to a source follower 90 to match the impedance of a connecting coaxial cable 92. The coaxial cable 92 from each sensor is attached to a 20 channel data acquisition system 94 with LeCroy 6810 digitizer modules. The system can sample 1 million samples per second, with a capacity of 128 thousand samples per channel. The data acquisition system 94 is connected to a 486 computer 96 with a 9600 baud modem 98.

Referring again to FIG. 2, in the above-referenced testing, the top 6 meters (20 feet) of each block was tested along five lines, only four of which are shown as 60, 61, 62, and 63 in FIG. 2. The vertical lines were spaced 3 meters (about 10 feet) apart, starting at 1.2 meters (about 4 feet) from the southern edge of the block. This portion of the dam has a rectangular shape which will ease data reduction efforts. The receivers 20 were placed in pairs along a vertical line on the downstream face of Barker Dam.

Figure 4:
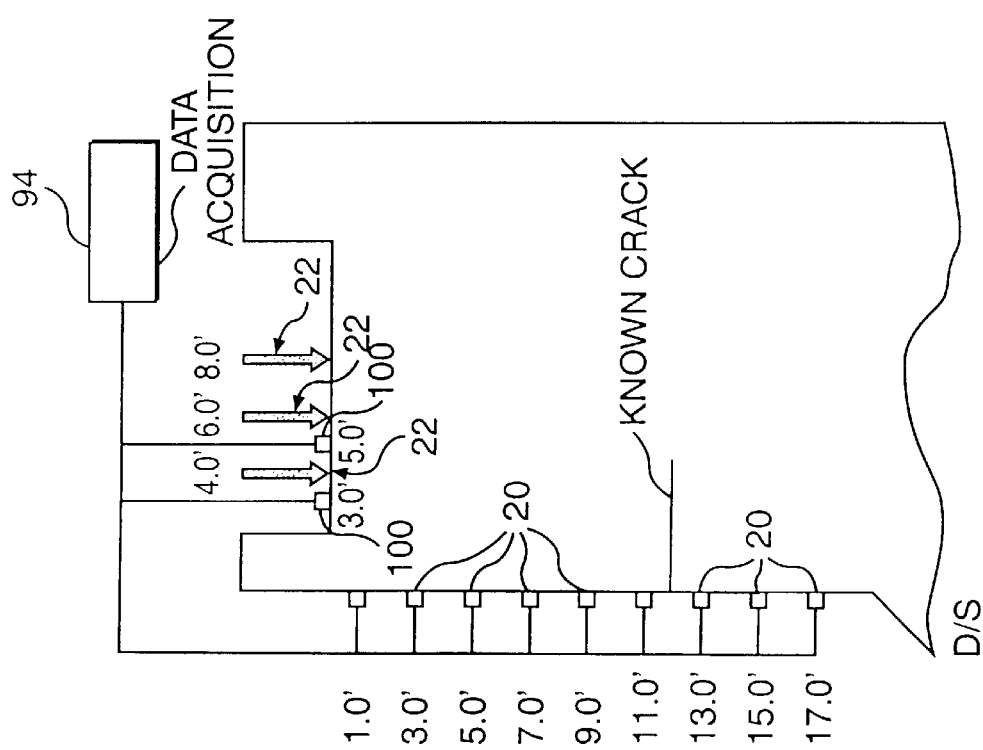
FIG. 4 is a further schematic representation illustrating a further aspect of the system of the invention.

In the testing being considered, receivers 20 were spaced on approximate 2 foot centers, as shown in FIG. 4. The sensors (not specifically shown) of receivers 20 were attached to the dam with petroleum jelly, then the leads (not shown) of each sensor were hot-glued to the dam 10. Additional receivers (sensors) denoted 100, were placed on the top of the dam, one at 0.9 meters (3 feet), and one at 1.5 meters (5 feet) from the downstream face. The wires from each sensor were bundled together with the wires from the other sensors so that the sensors would hang down at the appropriate intervals. The wire bundle was then connected to the data acquisition system 94 of FIG. 3. The data was stored on the 486 personal computer 96.

In an exemplary embodiment, the impact source or device 22 comprises a 3.6 kilogram (8 pound) sledge hammer with an accelerometer attached to one end thereof. In the testing referred to above, the hammer struck a 100 millimeter (4 inch) square metal plate, 25 millimeters (1 inch) thick. The location of the plate was typically placed at 1.2 meters, 1.8 meters, and 2.4 meters (4 feet, 6 feet and 8 feet) from the downstream face, and additional repeat impact was typically made at 2.4 meters (8 feet). Over 1800 data traces were gathered at Barker Dam. The data analysis comprised of the initial wave form analysis of selected arrival times. Then a tomographic image was created from the arrival times in the distances between the source and receiver locations.

Initially, the 1800 data traces were combined in groups of twenty, each group contained the waveforms of the twenty receivers 20 that matched a single impulse. These waveforms were then combined to form a waterfall plot. Then the traces were reviewed to remove anomalous records. The latter typically came from sensors that were malfunctioning and did not record a response to the impulse source 22.

Then for each group of twenty data traces, the time of first arrival for each wave was determined. Each wave was reviewed and the arrival time of the compressive wave was noted. At this point the travel time was computed. This was then combined with the distance between each sensor and the impact source to determine the wave velocity between the location of the impact source and each receiver.

The files containing the location of each source and receiver, and the corresponding velocities, were combined, and the time of arrival was analyzed using a tomography program running on the general purpose computer 96. This program was initially developed for analyzing seismic signals but modified to analyze the acoustic data through methods such as those described in Kepler, W. F. "Improved Assessment of Concrete Dams Using Acoustic Travel Time Tomography" Ph.D. Dissertation. University of Colorado at Boulder. The resulting tomograph is shown in FIG. 5.

In order to build a viable tomograph, a number of ray paths must be used. In one example, only two locations had enough ray paths to create valid tomographs. In addition, the tomographs have not been refined to remove edge effects, and thus a forward model should be performed as indicated below.

Figure 5:
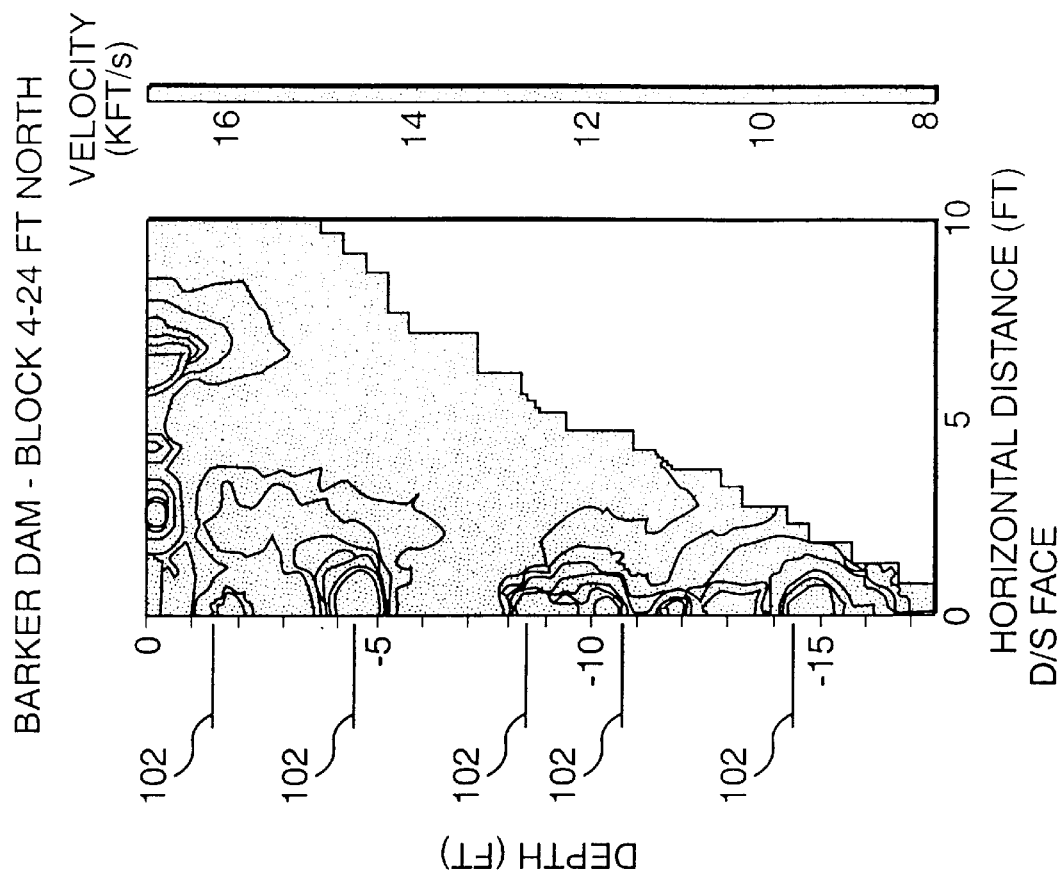
FIG. 5 is a graphical representation used in explanation of the operation of the system of the invention.

Turning to a comparison of acoustic travel time tomographs results and known conditions, in the testing at Barker Dam, the downstream face of Block 4 of Barker dam has five horizontal cracks, indicated 102 in FIG. 5, in the top 5 m (17 ft). The crack locations are shown in Table 1 below which provides comparisons between known horizontal crack locations and the tomographic estimate of the crack locations in the top 5 m (17 ft) of Block no. 4 of Barker Dam. The vertical distance from the top of the dam in meters (ft) are given.

TABLE 1

| Block 4-14 North | | Block 4-24 North | |
|---|---|---|---|
| Known Crack location | Tomographic estimate of crack location | Known Crack location | Tomographic estimate of crack location |
| 0.61 (2.0) | 0.91 (3.0) | 0.46 (1.5) | 0.55 (1.8) |
| 1.37 (4.5) | not apparent | 1.37 (4.5) | 1.40 (4.6) |
| 2.56 (8.4) | 2.52 (8.3) | 2.56 (8.4) | 2.62 (8.6) |
| 3.29 (10.8) | 3.29 (10.8) | 3.29 (10.8) | 3.20 (10.5) |
| 4.42 (14.5) | 4.42 (14.5) | 4.39 (14.4) | 4.39 (14.4) |

It will be appreciated the foregoing description of the Barker dam testing relates to earlier work and is merely exemplary. Improvements include the use of better computers to store and manipulate data and the use of the tomography computer program "3D-TOM" from the Bureau of Mines which can perform a laminar media reconstruction and which can incorporate previously established calibration data. Also, forward modeling using synthetic data can be used to determine the best locations for the source and receivers.

It will be understood from the foregoing that the method of the invention is a novel testing procedure which can characterize the physical properties of the unjointed concrete, and map lift-line delaminations. The sonic test results can be correlated with destructive tests to determine bulk strength and modulus. Such tests can be used to locate changes in the physical properties of the unjointed concrete within the dam. Using the method and system of the invention, lift-lines can be characterized and anomalies mapped. Further, the testing procedure of the invention provides a more comprehensive data set for use in the finite element model at a significantly reduced cost than is currently possible.

Although the present invention has been described in relation to specific exemplary embodiments thereof, it will be understood by those skilled in the art that variations in and modifications can be affected in these exemplary embodiments without departing from the scope and spirit of the invention.

What is claimed is:

1. An acoustic travel time tomography system for determining physical properties of a dam, said system comprising:
    a plurality of acoustic sensors, positioned on said dam at a plurality of fixed spaced sensor locations which are known relative to each other, for producing output data responsive to the detection thereby of acoustic waves generated in said dam;
    an impact source for producing an impact at an impact location which is known relative to said sensor locations so as to generate acoustic waves in the dam that pass through a portion of the dam for detection by said sensors; and
    data processing means for acquiring output data from said sensors produced responsive to acoustic waves generated by said impact source and for analyzing said output data and data related to the relative locations of the sensors and the impact source to determine the travel times of the acoustic waves to the sensors so as to determine physical properties of said dam.

2. An acoustic travel time tomography system according to claim 1 wherein said data processing means includes a computer.

3. An acoustic travel time tomography system according to claim 1 wherein said sensors are spaced apart approximately ten feet.

4. An acoustic travel time tomography system according to claim 1 wherein said impact source comprises an impactor and accelerometer connected to said impactor.

5. An acoustic travel time tomography system according to claim 4 further comprising a plate positioned on said dam for striking by said impactor.

6. An acoustic travel time tomography system according to claim 5 wherein said impactor comprises a sledge hammer.

7. An acoustic travel time tomography system according to claim 4 wherein said impactor produces impacts at a frequency between 1 and 50 kilohertz.

8. An acoustic travel time tomography system according to claim 5 wherein said impactor comprises a 3.6 kilogram sledge hammer and said plate is 100 millimeters square and 25 millimeters thick.

9. Acoustic travel time tomography system according to claim 1 wherein said sensors are located on two different surfaces of the dam and one of said surfaces comprises a dam face.

10. Acoustic travel time tomography system according to claim 1 wherein said data processing means stores the output data from the sensors, groups the output data into sets, removes erroneous data from the sets, and forms a tomographic map of the physical anomalies.

11. A method for determining physical properties of a concrete dam having a surface, said method comprising the steps of:
    positioning a plurality of acoustic sensors on said surface of said dam at sensor locations which are spaced apart at known distances relative to each other so that said sensors can receive sonic waves produced in said dam and can produce output data responsive thereto;
    positioning an impact means for impacting said dam at an impact position which is known relative to said sensor locations;
    activating said impact means to generate a plurality of sonic waves in said dam that pass through the dam and are received by said plurality of sensors; and
    monitoring the output data produced by said sensors to detect which of said sensors receive said sonic waves and to determine, based on the known relative positions of said sensors and said impact means, travel times of the sonic waves to the sensors receiving said sonic waves so as to determine the locations of physical anomalies in said dam.

12. A method according to claim 11 further comprising repositioning said impact means at different locations on said surface of said dam.

13. A method according to claim 11 wherein monitoring of said sensors comprises storing said output data produced by said sensors on a computer, grouping said output data into sets, removing erroneous data from said sets, and forming a tomographic map of said physical anomalies.

14. A method according to claim 11 wherein said monitoring of said sensors further comprises determining the time of first arrival of each of said sonic waves, reviewing each wave to determine the time of arrival of a corresponding compressive wave, and computing the travel time of said compressive wave to produce a computed travel time.

15. A method according to claim 11 further comprising correlating the results of determining said physical anomalies with destructive strength test results.

16. A method according to claim 15 wherein said destructive strength test results are produced by core sampling.

17. A method according to claim 11 wherein said sonic waves are generated by impacting the dam with an impactor at an impact frequency rate between 1 and 50 kilohertz.

18. A method according to claim 11 further comprising mapping areas surrounding previously determined locations of physical anomalies with a second plurality of sensors positioned more closely together than the first mentioned plurality of sensors.

19. A method according to claim 11 wherein said sensors are positioned on two different surfaces of the dam and one of the surfaces comprises a dam face.

20. A method for determining physical properties of a concrete dam having a surface, said method comprising the steps of:

positioning a plurality of acoustic sensors on said surface of said dam at sensor locations which are spaced apart at known distances relative to each other so that said sensors can receive sonic waves produced in said dam and can produce output data responsive thereto;

positioning an impact means for impacting said dam at an impact position which is known relative to said sensor locations;

activating said impact means to generate a plurality of sonic waves in said dam so that said sonic waves can be received by said plurality of sensors; and monitoring the output data produced by said sensors to detect which of said sensors receive said sonic waves and to determine, based on the known relative positions of said sensors and said impact means, travel times of the sonic waves to the sensors receiving said sonic waves so as to determine the locations of physical anomalies in said dam, said monitoring of said sensors further comprising determining the time of first arrival of each of said sonic waves, reviewing each wave to determine the time of arrival of a corresponding compressive wave, computing the travel time of said compressive wave to produce a computed travel time, and using said computed travel time and the distances between said impact position and said sensor positions to determine the wave velocity of the sonic waves traveling between said impact position and said sensor positions.

* * * * *